(12) United States Patent
Mohr et al.

(10) Patent No.: US 6,235,940 B1
(45) Date of Patent: May 22, 2001

(54) METHOD FOR PRODUCING OXALKYLATED AMINES OR ALCOHOLS

(75) Inventors: Juergen Mohr, Gruenstadt; Toni Dockner, Meckenheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/581,233

(22) PCT Filed: Dec. 17, 1998

(86) PCT No.: PCT/EP98/08302

§ 371 Date: Sep. 11, 2000

§ 102(e) Date: Sep. 11, 2000

(87) PCT Pub. No.: WO99/33783

PCT Pub. Date: Jul. 8, 1999

(30) Foreign Application Priority Data

Dec. 23, 1997 (DE) ............................................. 197 57 709

(51) Int. Cl.[7] ................................................. C07C 209/28
(52) U.S. Cl. ............................................. 564/468; 568/319
(58) Field of Search ............................. 564/468; 568/319

(56) References Cited

U.S. PATENT DOCUMENTS 3,313,846 * 4/1967 Slovinsky ............................ 502/170

FOREIGN PATENT DOCUMENTS

| 19502970 | * 8/1996 | (DE) | ............................. C08G/65/20 |
| 195 44 739 | 6/1997 | (DE) . | |
| WO 91/15441 | * 10/1991 | (WO) | ............................. C07B/41/04 |
| WO 94/09055 | * 4/1994 | (WO) | ............................. C08G/65/10 |

OTHER PUBLICATIONS

Nikolaus Schoenfeldt, Grenzflaechenaktive Aethylenoxid–Addukte, pp. 15–33, "Reaktionsmechanismus", 1976.

Nikolaus Schoenfeldt, Grenzflaechenaktive Aethylenoxid–Addukte, pp. 83–101, "Verschiedene Arbeitsmethoden", 1976.

* cited by examiner

Primary Examiner—Johann Richter
Assistant Examiner—Brian J. Davis
(74) Attorney, Agent, or Firm—Oblon, Spivak, McClelland, Maier & Neustadt, P.C.

(57) ABSTRACT

In a process for preparing alkoxylated amines or alcohols in which a reaction mixture comprising an amine or an alcohol or a mixture of two or more amines and/or alcohols and an alkylene oxide, or a mixture of two or more different alkylene oxides, is reacted in one or more successive reaction steps, at least one of the reaction steps is carried out in the presence of a basic catalyst and, in at least one of the reaction steps, formic acid or a salt of formic acid or a mixture of two or more thereof is present in the reaction mixture or the reaction mixture is admixed with formic acid or a salt of formic acid, or a mixture of two or more thereof, after the alkoxylation is complete. The alkoxylates prepared by the process of the present invention have a light color and a low odor.

10 Claims, No Drawings

METHOD FOR PRODUCING OXALKYLATED AMINES OR ALCOHOLS

This application is a 371 of PCT EP98/08302 filed Dec. 17, 1998.

The present invention relates to a process for preparing alkoxylated amines or alcohols or mixtures thereof, in which an amine or a mixture of two or more amines, or an alcohol or a mixture of two or more alcohols, or a mixture of one or more amines and one or more alcohols, is reacted with an alkylene oxide, or a mixture of two or more different alkylene oxides, in one or more successive reaction steps.

The reaction products of amines or alcohols with alkylene oxides are known as surface-active and interface-active compounds and are employed in a wide variety of industrial fields. Particular examples are laundry detergents and cleaners, personal care products or industrial applications, for example use as emulsifiers, dispersants, emulsion breakers or dispersion breakers, or as intermediates, thickeners or lubricants.

Processes known from the prior art for alkoxylating amines are generally carried out in one or two stages, while single-stage processes are generally preferred for the alkoxylation of alcohols.

Thus, for example, DE-A 195 44 739 describes a process for preparing alkoxylated polyethylenimines by alkoxylation of polyethylenimines in one or two process steps to give reaction products which contain from 1 to 200 mol of alkylene oxide groups per amino group in the polyethylenimine. In the single-stage procedure, anhydrous polyethylenimines and from 1 to 20 mol %, based on polyethylenimines, of at least one anhydrous base are initially placed in the reaction vessel or aqueous solutions of these materials are dried and after removal of all the water at >135 to 150° C. reacted with at least one alkylene oxide. In the two-stage procedure, polyethylenimine is reacted in the first process step at from 80 to 100° C. with from 0.7 to 0.9 mol, based on 1 mol of amino groups in the polymer, of at least one alkylene oxide in aqueous solution, and in the second process step the reaction product obtained in the first process step is reacted at from 120 to 150° C. with at least one alkylene oxide in the absence of water and in the presence of from 1 to 20 mol %, based on polyethylenimine, of an alkaline catalyst to give alkoxylated polyethylenimines containing from 1 to 200 mol of alkylene oxide groups per amino group in the polyethylenimine. Light-colored or virtually colorless products are, according to this publication, only obtained when a high catalyst concentration is employed. The publication gives no information about the olfactory properties of the resulting product.

Suggestions for suitable reaction conditions in the preparation of interface-active alkoxylation products may be found, for example, in N. Schönfeldt, Grenzflächenaktive Äthylenoxid-Addukte, Wissenschaftliche Verlagsgesellschaft mbH, Stuttgart, 1976, p. 15 ff. and p. 83 ff.

However, under the alkoxylation conditions customarily selected, by-products whose type, number and amount may differ depending on the process variant selected are formed in addition to the actual alkoxylation products. For example, carbonyl compounds such as acetaldehyde (as a rule when using ethylene oxide) or higher aldehydes and also their downstream products are frequently formed, and these can influence the color and odor of the alkoxylation product.

The alkoxylated amines and alcohols, in particular the abovementioned polyethylenimines, obtainable by the methods described in the prior art can therefore, depending on the degree of alkoxylation, be strongly discolored and have an extremely unpleasant odor, or it is necessary to work under uneconomical process conditions, for example using large amounts of catalyst, in order to reduce the discoloration.

Attempts to at least substantially remove the compounds causing the discoloration and odor afterwards, e.g. by oxidative or reductive bleaching or by stripping, for example using nitrogen or steam, also generally do not lead to the desired success.

It is an object of the present invention to provide a process for the alkoxylation of amines or alcohols or mixtures thereof which leads to products which have very little discoloration and additionally have only a very small proportion of compounds which cause undesirable odors.

We have found that this object is achieved by carrying out the alkoxylation in the presence of formic acid or a salt of formic acid or a mixture of two or more thereof.

The present invention accordingly provides a process for preparing an alkoxylated amine or a mixture of two or more alkoxylated amines, or an alkoxylated alcohol or a mixture of two or more alkoxylated alcohols, or a mixture of one or more alkoxylated amines and one or more alkoxylated alcohols, in which a reaction mixture comprising an amine or a mixture of two or more amines, or an alcohol or a mixture of two or more alcohols, or a mixture of one or more amines and one or more alcohols, and an alkylene oxide, or a mixture of two or more alkylene oxides is reacted in one or more successive reaction steps, wherein at least one of the reaction steps is carried out in the presence of a basic catalyst and wherein formic acid or a salt of formic acid, or a mixture of two or more thereof is present in the reaction mixture in at least one of the reaction steps, so as to give an alkoxylated reaction product.

For the purposes of the present invention, the term "reaction step" means an overall reaction after which an isolable product or intermediate which undergoes no further reactions (with the possible exception of secondary reactions proceeding at a low rate) is present. The process of the present invention can therefore proceed, for example, in a single "reaction step" regardless of how many individual reaction events actually occur in the reaction mixture provided that the desired end product is present after the conclusion of the reaction. However, the process of the present invention can also be carried out in a plurality of steps, i.e. individual steps leading to the desired end product can be carried out sequentially so that the completion of the first step is followed by a second step which can, at a later point in time, be carried out in the same reaction vessel or in a different reaction vessel. If appropriate, this can be followed by further steps until the desired end product has been obtained.

In the process of the present invention, it is possible, for example, to subject any compounds which bear at least one amino group (amines) to an alkoxylation, where the amines can be compounds which can have one or more primary or secondary amino groups and, if desired, additionally one or more tertiary amino groups. Mixtures of two or more such compounds can just as well be subjected to the process of the present invention. The process of the present invention is accordingly not restricted to the reaction of compounds having only one amino group, but it is also possible, for example, to use diamines or polyamines. Examples of suitable amines are ammonia, methylamine, ethylamine, 1-propylamine, 2-propylamine, 1-butylamine, 2-butylamine, 1-pentylamine, 2-pentylamine, 3-pentylamine, the corresponding isomeric hexylamines, heptylamines, octylamines, nonylamines, decylamines and also higher linear or branched alkylamines which are obtainable, for example, by amination of fatty alcohols having up to 24 carbon atoms. Likewise suitable are the corresponding secondary amines of the abovementioned compounds as are obtainable, for example, by monoalkylation of the compounds mentioned. Examples are dimethylamine, N-methylethylamine, N-diethylamine, N-methylpropylamine, N-methylbutylamine, N-methylpentylamine, N-methylhexylamine and the like.

Further suitable compounds are oligoamines which have at least two amino groups per molecule. These include, for example, ethylenediamine, propylenediamine, butylenediamine, pentamethylenediamine, hexamethylenediamine, heptamethylenediamine, octamethylenediamine and the like; this listing is intended to encompass any positional isomers of the compounds mentioned. The process of the present invention can likewise be carried out using amines which have both primary and secondary and, if desired, additionally one or more tertiary amino groups in one molecule. These include, for example, N-methylethylenediamine, N-ethylethylenediamine, N-methylpropylenediamine, N-ethylpropylenediamine, N-methylbutylenediamine, N-ethylbutylenediamine, N-methylpentamethylenediamine, N-methylhexamethylenediamine and the like, and also their higher homologues for example N-monoalkylated diamines having up to 26 carbon atoms, which may be linear or branched. Likewise suitable are amines which have a differing number of primary, secondary and, if desired, tertiary amino groups in one molecule. These include, for example, diethylenetriamine, triethylenetetramine, tetraethylenepentamine, N-(3-aminopropyl)ethylenediamine, N-(4-aminobutyl)ethylenediamine, N-(4-aminobutyl)propylenediamine and the like.

Further suitable amines are compounds selected from the group of polyethylenimines having a weight average molecular weight ($M_W$) of, for example, from 250 to 2,000,000, preferably from about 580 to about 10,000. Such polyethylenimines are generally prepared by polymerization of ethylenimine in aqueous medium in the presence of acid catalysts. Examples of suitable acid catalysts are mineral acids such as hydrochloric acid, sulfuric acid, phosphoric acid, hydrobromic acid and hydroiodic acid and also organic acids such as formic acid, acetic acid and propionic acid, amidosulfonic acid, p-toluenesulfonic acid and benzenesulfonic acid, sodium hydrogen sulfate, potassium hydrogen sulfate, addition products of sulfuric acid onto ethylenediamine and addition products of carbon dioxide onto ethylenediamine. Also suitable are alkylating agents such as methyl chloride, ethyl chloride, propyl chloride, lauryl chloride and benzyl chloride, and also Lewis acids such as boron trifluoride. The amount of acid catalysts, based on ethylenimine, is, for example, less than 1% by weight and is preferbaly in the range from 0.01 to 1% by weight. In a preferred embodiment of the present invention, polyethylenimine having a molecular weight $M_W$, of from 600 to 6000 is subjected to an alkoxylation according to the present invention.

It is particularly advantageous for formic acid to have been used in the preparation of the polyethylenimine. In a preferred embodiment of the invention, polyethylenimine having a molecular weight $M_W$, of from 600 to 6000 which has been prepared using formic acid is therefore subjected to an alkoxylation according to the present invention.

In the process of the present invention, it is also possible to subject compounds which bear at least one OH group (alcohols) to an alkoxylation, where the alcohols can be compounds which each have one or more primary or secondary or tertiary OH groups, or at the same time two or more of the various OH groups mentioned. Mixtures of two or more such compounds can just as well be subjected to the process of the present invention. The process of the present invention is accordingly not restricted to the reaction of compounds having only one OH group (monoalcohols), but it is also possible to use, for example, dialcohols or polyalcohols. For example, linear, branched or cyclic aliphatic $C_{1-44}$-alcohols having from one to about ten OH groups are suitable for use in the process of the present invention. Likewise suitable are monocyclic or polycyclic, aromatic or heteroaromatic $C_{6-40}$-alcohols having from one to about ten OH groups, where the aromatic or heteroaromatic alcohols may, for example, have aliphatic or cycloaliphatic substituents or parts of the ring framework can be cycloaliphatic. Likewise suitable are, for example, polymers bearing OH groups, as are obtainable, for example, by polymerization, polyaddition or polycondensation.

Examples of suitable monoalcohols are methanol, ethanol, propanol, isopropanol, 1-butanol, 2-butanol, tert-butanol, the isomeric pentanols, hexanols, heptanols, octanols, for example 2-ethylhexanol, the linear and branched $C_{9-24}$-fatty alcohols as are obtainable, for example, by the oxo process, cycloaliphatic alcohols, for example cyclohexanol, cycloheptanol, cyclooctanol, hydroxymethylcyclohexane, hydroxymethylcycloheptane, hydroxymethylcyclooctane, monohydroxyaromatics and substituted monohydroxyaromatics, for example phenol, methylphenol, ethylphenol, propylphenol, butylphenol and their alkyl homologs, for example octylphenol or nonylphenol, and the like. Examples of suitable diols are ethylene glycol, 1,2-propylene glycol, 1,3-propylene glycol, 1,2-butylene glycol, 1,3-butylene glycol, 1,4-butylene glycol, the isomeric pentylene glycols and hexylene glycols, for example 1,6-hexanediol, and their higher homologs, o-, m- and p-dihydroxybenzene, o-, m- and p-bis(hydroxymethyl)benzene, 4,4'-dihydroxybiphenyl, bisphenol A and also the products of partial or complete hydrogenation of the aromatic double bonds of the compounds mentioned.

Likewise suitable are higher alcohols having up to about 10 OH groups, in particular from about 3 to about 6 OH groups, for example glycerol, trimethylolpropane, triethylolpropane, pentaerythritol or carbohydrates such as sorbitol. Also suitable are the condensation products (monoethers and polyethers) of the abovementioned compounds with themselves or of two or more of the compounds mentioned with one another, having up to about 20 or 30 OH groups. OH-containing polymers, as can be used for the purposes of the present invention, include, for example, polyvinyl alcohol or hydroxyl-containing polyacrylates which are obtainable by, for instance, homopolymerization or copolymerization of OH-containing acrylic esters.

For the purposes of the present invention, the term "alkoxylation" refers to the reaction of one of the abovementioned amines, or a mixture of two or more of the abovementioned amines, or one of the abovementioned alcohols or a mixture of two or more of the abovementioned alcohols or a mixture of one or more of the abovementioned amines and one or more of the abovementioned alcohols with an alkylene oxide, or a mixture of two or more different alkylene oxides.

The alkylene oxides which can be used for the alkoxylation in the process of the present invention are preferably alkylene oxides of the formula I

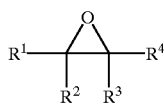
(I)

where $R^1$, $R^2$, $R^3$ and $R^4$ are identical or different and are each, independently of one another, hydrogen, $C_{1-10}$-alkyl, $C_{2-10}$-alkenyl, $C_{2-10}$-alkynyl, $C_{3-10}$-cycloalkyl, $C_{3-10}$-cycloalkenyl, $C_{6-12}$-aryl or heteroaryl, where the alkyl, alkenyl or alkynyl radicals may be linear or branched and may in turn bear further functional groups, and the cycloalkyl, aryl and heteroaryl radicals may in turn bear further functional groups or be substituted by $C_{1-10}$-alkyl, alkenyl, alkynyl or aryl radicals.

Alkylene oxides of the formula I which are preferably used are, for example, ethylene oxide, propylene oxide, isobutylene oxide, 1,2-butylene oxide, 2,3-butylene oxide, pentylene oxide or styrene oxide, or mixtures of two or more thereof, with preference being given to ethylene oxide, propylene oxide or 1,2-butylene oxide or mixtures of two or more thereof.

The alkylene oxide or mixture of two or more different alkylene oxides which can be used in the present process can originate from any source or from any different sources, i.e. can have been prepared by any desired process. For example, ethylene oxide can be obtained by catalytic oxidation of ethylene, where ethylene and a gas comprising molecular oxygen, for example air, oxygen-enriched air or pure oxygen, are reacted in the gas phase over a silver-containing catalyst. The alkylene oxide or mixture of two or more different alkylene oxides which can be used for the purposes of the present invention is preferably used in pure form. This means that the alkylene oxides used are essentially free of impurities and thus consist of essentially 100% of the alkylene oxide or the mixture of two or more different alkylene oxides. However, it is likewise possible to use a technical grade of alkylene oxides which still contains impurities which are usually present prior to purification of the alkylene oxide after its production.

The alkoxylation can be carried out using only a single type of alkylene oxide, but it can also be a mixed alkoxylation. If, for example, a mixture of two or more different alkylene oxides is introduced into the reaction mixture, this generally leads, if the reactivities of the alkylene oxides are essentially comparable, to random polyether chains in which the constituents of the mixture are not present in any particular order. However, if the different alkylene oxides are fed into the reaction mixture in succession, i.e. a further alkylene oxide intended for the reaction is only fed in when that previously fed in has reacted completely, polyether segments made up of blocks and in which the order and length of the individual alkylene oxide segments in the polyether chain is dependent on the order of addition of the respective alkylene oxide and its amount can be obtained.

In a preferred embodiment of the invention, the ratio of alkylene oxide groups to acidic hydrogen atoms bound to nitrogen in the amine or in the mixture of two or more amines, or in the alcohol or in the mixture of two or more alcohols, or in the mixture of one or more amines and one or more alcohols, is from about 1:1 to about 300:1.

The basic catalyst used in the process of the present invention is generally an alkaline compound customarily used for base-catalyzed reactions, for example alkali metal hydroxides such as lithium hydroxide, sodium hydroxide, potassium hydroxide or cesium hydroxide, alkali metal alkoxides such as sodium or potassium methoxide, potassium ethoxide, potassium isopropoxide or potassium tert-butoxide or mixtures of two or more thereof.

In place of the potassium alkoxides mentioned, it is also possible to use the corresponding sodium alkoxides. Further suitable basic catalysts are sodium hydride and heterogeneous catalysts, for example hydrotalcite which may be modified or unmodified, or mixtures thereof. The amount of basic catalyst in the reaction mixture can be from about 0.1 to about 20 mol %, based on acidic hydrogen atoms bound to nitrogen in the amine or in the mixture of two or more amines, or in the alcohol or in the mixture of two or more alcohols, or in the mixture of one or more amines and one or more alcohols. It is preferably from about 1 to about 10 mol % and particularly preferably from about 2 to about 5 mol %.

The process of the present invention can be carried out in one or more successive reaction steps, with formic acid or a salt of formic acid, or a mixture of two or more thereof, being present in the reaction mixture in at least one of the reaction steps.

In a particularly preferred embodiment, the formic acid or the salt of formic acid, or a mixture of two or more thereof, is present in the reaction mixture at the beginning of the alkoxylation.

As salts of formic acid, it is possible in principle to use all salts, but alkali metal formates, for example the formates of lithium, sodium or potassium, or ammonium formates as are obtainable, for example, from formic acid and ammonia or organic amines are particularly suitable as salts of formic acid. Particular preference is given to sodium formate and potassium formate.

The formic acid or the salt of formic acid, or a mixture of two or more thereof, is generally used in the process of the present invention in an amount of from about 0.1 to about 10 mol %, based on acidic hydrogen atoms bound to nitrogen in the amine or in the mixture of two or more amines, or in the alcohol or in the mixture of two or more alcohols, or in the mixture of one or more amines and one or more alcohols. In preferred embodiments of the invention, use is made, for example, of amounts of from about 0.5 to about 8 mol %, for example from about 1 to about 6 mol % or from about 2 to about 5 mol %. Amounts of, for example, from about 3 to about 4 mol % are likewise suitable.

The process of the present invention can, for example, be carried out in one step. Here, a reaction mixture comprising an amine or a mixture of two or more amines, or an alcohol or a mixture of two or more alcohols, or a mixture of one or more amines and one or more alcohols, a basic catalyst, formic acid or a salt of formic acid or a mixture of two or more thereof, together with an alkylene oxide, or a mixture of two or more different alkylene oxides, is reacted. The reaction is, in a preferred embodiment, carried out at from about 80° C. to about 170° C.

A single-stage reaction procedure is preferred when the reaction mixture is essentially free of water, i.e. the water content of the reaction mixture is less than 1000 ppm, preferably less than 500 ppm.

To achieve such a water content, it is possible, for example, to use the individual constituents of the reaction mixture in essentially water-free form. However, it is likewise possible to free the reaction mixture of water prior to the reaction if, for example, one or more of the components present in the reaction mixture has a water content which is too high. This can be achieved, for example, by distilling all of the water from the reaction mixture. For this purpose, the reaction mixture is generally subjected to either reduced pressure or elevated temperature or preferably both at the same time, so that water present in the reaction mixture distills off. Care needs to be taken that none of the further components which are present in the reaction mixture and are intended for the reaction distill off together with the water. If, for example, components whose boiling point is below that of water or which form an azeotrope together with water are present in the reaction mixture, it is advisable to use these compounds in essentially water-free form and to remove any water present in the reaction mixture in the manner described before they are added. The removal of water can also be carried out, for example, by means of an azeotropic distillation by adding an entrainer such as benzene, toluene or xylene and removing the water azeotropically. The entrainer added can subsequently be distilled off under reduced pressure or can remain in the reaction mixture during the alkoxylation.

When the process of the present invention is carried out in a single step, the reaction temperature is preferably from about 100 to 160° C., for example from about 120 to about 135° C. or from about 135 to about 150° C. The reaction time is generally from about 4 to about 20 hours, for example from about 8 to about 12 hours.

The single-stage procedure is, in a preferred embodiment of the invention, employed especially in the alkoxylation of alcohols.

In a further preferred embodiment of the invention, the reaction is carried out in two steps, where a) in a first step, a reaction mixture comprising an amine or a mixture of two or more amines, or an alcohol or a mixture of two or more alcohols, or a mixture of one or more amines and one or more alcohols, formic acid or a salt of formic acid, or a mixture of two or more thereof, together with an alkylene oxide, or a mixture of two or more different alkylene oxides, is reacted to form a reaction product of the first step, and b) in a second step, a reaction mixture comprising the reaction product of the first step, a basic catalyst and an alkylene oxide, or a mixture of two or more different alkylene oxides, is reacted.

The reaction temperature is, for example, from about 80° C. to about 130° C. in the first step and, for example, from more than about 130° C. to about 170° C. in the second step.

The two-stage procedure for the process of the present invention is employed, in particular, when the reaction mixture comprises an amine or a mixture of two or more amines.

When an amine or a mixture of two or more amines is to be reacted in the process of the present invention, the reaction mixture in the first step comprises, in a preferred embodiment of the invention, the amine or the mixture of two or more amines as an aqueous solution. Here, it is preferred that the amine or the mixture of two or more amines is present in the aqueous solution in a concentration of from about 20% by weight to about 80% by weight, in particular from about 40% by weight to about 60% by weight. The further components present in the reaction mixture of the first step can likewise be used in the form of their aqueous solutions, for example the basic catalyst can be used as a solution having a concentration of from about 20 to about 80% by weight, preferably from about 40 to about 60% by weight. Of course, the same also applies to the formic acid or the salt of formic acid, or the mixture of two or more thereof. In a preferred embodiment of the invention, water is removed essentially completely from the reaction product of the first step before the second step is carried out.

The use of at least one of the components present in the reaction mixture as aqueous solution is advantageous when all components of the reaction mixture are soluble in water. If one or more of the components present in the reaction mixture does not have sufficient solubility in water, it is generally preferred that the process of the present invention is not carried out using aqueous solutions. A component is sufficiently soluble in water if the component dissolves at least partially, preferably predominantly, in water at the reaction temperature.

If desired, the process of the present invention can also be carried out in organic solvents or completely without solvents. Suitable organic solvents are, in particular, all polar, aprotic solvents, for example dimethylformamide (DMF) or dimethylacetamide (DMAc), but preference is given to using no solvents. Use of no solvents is a possibility when, in particular, the compound to be alkoxylated or the mixture of compounds to be alkoxylated is in the liquid state at the reaction temperature.

The reaction temperature in the first step is from about 80 to about 130° C., preferably from about 80 to about 100° C. The reaction time in the first step is, for example, from about 2 to about 12 hours, preferably from about 4 to about 8 hours.

The molar ratio of alkylene oxide groups to acidic hydrogen atoms bound to nitrogen in the amine or in the mixture of two or more amines, or in the alcohol or in the mixture of two or more alcohols, or in the mixture of one or more amines and one or more alcohols, can be, for example, about 1:1 in the first step. However, it has been found that the color of the product formed is additionally affected in an advantageous way if a ratio of less than 1, for example from about 0.4:1 to about 0.99:1, particularly preferably from about 0.6:1 to about 0.9:1, is selected.

The first step can be carried out under atmospheric pressure, but the reaction may also be carried out in an autoclave at pressures of up to about 20 bar.

In the second step, a reaction mixture comprising the reaction product of the first step, a basic catalyst and an alkylene oxide, or a mixture of two or more different alkylene oxides, is reacted at from >130° C. to about 170° C. To prepare for the second step, the procedure can be, for example, firstly to evaporate the reaction product obtained in the first process step to dryness, if a solvent has been used and the reaction product itself is not liquid, and subsequently to add the basic catalyst.

If the first process step has been carried out in aqueous solution, it is particularly preferred to add the basic catalyst to the aqueous reaction product obtained in the first reaction step and subsequently to remove the water, e.g. by distillation under reduced pressure or by means of an azeotropic distillation by adding, for example, an extrainer such as benzene, toluene or xylene and removing the water azeotrope.

The alkoxylation in the second process step is carried out at from more than about 130° C. to about 170° C., preferably in the range from more than about 130° C. to about 145° C. The reaction can be carried out under atmospheric pressure or preferably under superatmospheric pressure. It is preferably carried out in an autoclave provided with a stirrer at pressures of from about 1 to about 20 bar, preferably from about 2 to about 10 bar.

The amount of alkylene oxide, or of a mixture of two or more different alkylene oxides, in the second step is set so that the product formed is an alkoxylated amine or a mixture of two or more alkoxylated amines, or an alkoxylated alcohol or a mixture of two or more alkoxylated alcohols, or a mixture of one or more alkoxylated amines and one or more alkoxylated alcohols, which has from about 1 to about 200 mol of alkylene oxide groups per acidic hydrogen atom bound to nitrogen in the amine or in the mixture of two or more amines, or in the alcohol or in the mixture of two or more alcohols, or in the mixture of one or more amines and one or more alcohols.

The alkoxylated products formed in the second process step preferably contain from about 1 to about 20 mol of reacted alkylene oxide, or a mixture of two or more different reacted alkylene oxides, per acidic hydrogen atom bound to nitrogen in the amine or in the mixture of two or more amines, or in the alcohol or in the mixture of two or more alcohols, or in the mixture of one or more amines and one or more alcohols. The reaction time in the second process step is from about 2 to about 15 hours and is preferably in a range from about 5 to about 12 hours.

In a preferred embodiment of the invention, the alkoxylated reaction product is maintained at from 40° C. to 140° C. and a pressure of from 0.1 to 100 mbar for a period of from 5 minutes to 5 hours after conclusion of the reaction, by which means, for example, volatile compounds can be removed.

The process of the present invention generally gives alkoxylated products which have a lighter color and a better odor compared to the products known from the prior art, with the amount of catalyst required being able to be reduced significantly below that required in the processes known from the prior art by the use according to the present invention of formic acid or salts of formic acid.

The invention is illustrated by the following examples, but without the examples implying any restriction of the scope of the invention.

EXAMPLES

Example 1

$1^{st}$ Step:

1470 g of an aqueous, 50% strength solution of a polyethylenimine (corresponding to 17.1 mol of acidic hydrogen atoms bound to nitrogen) were placed in a stainless steel autoclave having a capacity of about 20 l. 8 g of formic acid were subsequently added. The reactor was closed and flushed with nitrogen. It was then heated while stirring to 100° C. and 748 g (17 mol) of ethylene oxide were added at this temperature at a maximum pressure of 5 bar over a period of from 2 to 3 hours. After the addition was complete and a constant pressure had been reached, the reaction mixture was held at 100° C. for another 2 hours, after which it was cooled to 50° C. and depressurized.

$2^{nd}$ Step:

The reaction product obtained from the first step was admixed in the same reactor with 74 g of 50% strength, aqueous KOH solution. The reactor was closed, evacuated to a pressure of 20 mbar and slowly heated to 100° C. To remove most of the water from the reaction mixture, the reactor was maintained under these conditions for 6 hours.

Nitrogen was subsequently admitted into the reactor and, over the course of about 10 hours, 14,300 g (325 mol) of ethylene oxide were metered in at 140° C. and a maximum pressure of 5 bar. After addition was complete and a constant pressure had been reached, the mixture was stirred for another 2 hours at 140° C. The reactor was subsequently slowly depressurized to atmospheric pressure and cooled to about 80° C.

The reactor was then evacuated to from about 20 to 50 mbar and left under these conditions for 1 hour to remove volatile constituents. It was subsequently cooled to room temperature, depressurized and emptied. The yield was 15,800 g of ethoxylate having an average degree of ethoxylation of about 20. The product obtained is a yellow oil which slowly solidifies at room temperature and has a weak odor. The color number in 10% strength aqueous solution is 2 (iodine color number).

If the experiment is carried out without the addition according to the present invention of formic acid, the end product obtained is an amber-colored oil which slowly solidifies and has an iodine color number (10% strength in water) of 8. It has a sharp, very unpleasant odor.

The difference in odor of the two products can be demonstrated even more clearly by smelling a 0.5 or 1% strength aqueous solution. While the product of the present invention has only a weak odor, the comparative product has a sharp and acrid smell.

Example 2 a) Comparative Example Using a Conventional Procedure:

2300 g of isononylphenol were placed together with 2.5 g of potassium hydroxide in a reactor suitable for alkoxylation. The reactor was closed and the mixture was heated to 140° C., with vacuum being applied at the same time. The mixture was dried in this way for 2 hours at 30 mbar and nitrogen was subsequently admitted.

At 140° C. and a pressure of about 5 bar, 2580 g of ethylene oxide were then metered in over the course of from 3 to 4 hours. After the metered addition was complete, the mixture was stirred further for about 2 hours to complete the reaction. The mixture was subsequently maintained at about 20 to 50 mbar and from about 100 to 140° C. to remove any volatile constituents present. After cooling and emptying the reactor, about 4800 g of the ethoxylate having a color number of 67 (APHA) and a distinct aldehyde odor are obtained.

b) Process of the Present Invention

The experiment was repeated using process parameters identical to those indicated in a) except that 2.5 g of potassium formate were added to the isononylphenol/potassium hydroxide mixture at the beginning.

The alkoxylate obtainable in this way was distinctly lighter in color than that obtained in a), as could be seen by direct comparison. It had a color number of 35 (APHA) and an only barely perceptible odor.

What is claimed is:

1. A process for preparing an alkoxylated amine or a mixture of two or more alkoxylated amines, or an alkoxylated alcohol or a mixture of two or more alkoxylated alcohols, or a mixture of one or more alkoxylated amines and one or more alkoxylated alcohols, in which a reaction mixture comprising an amine or a mixture of two or more amines, or an alcohol or a mixture of two or more alcohols, or a mixture of one or more amines and one or more alcohols, and an alkylene oxide or a mixture of two or more alkylene oxides is reacted in one or more successive reaction steps, wherein at least one of the reaction steps is carried out in the presence of a basic catalyst and wherein formic acid or a salt of formic acid or a mixture of two or more thereof is present in the reaction mixture in at least one of the reaction steps, so as to produce an alkoxylated reaction product.

2. A process as claimed in claim 1, wherein the formic acid or the salt of formic acid, or a mixture of two or more thereof, is present in the reaction mixture at the beginning of the alkoxylation.

3. A process as claimed in claim 1, wherein the formic acid or the salt of formic acid, or a mixture of two or more thereof, is used in an amount of from 0.1 to 10 mol %, based on the total amount of acidic hydrogen atoms bound to nitrogen in the amine or in the mixture of two or more amines, or in the alcohol or in the mixture of two or more alcohols, or in the mixture of one or more amines and one or more alcohols.

4. A process as claimed in claim 1, wherein the molar ratio of alkylene oxide groups to acidic hydrogen atoms bound to nitrogen in the amine or in the mixture of two or more amines or in the alcohol or in the mixture of two or more alcohols or in the mixture of one or more amines and one or more alcohols is from 1:1 to 300:1.

5. A process as claimed in claim 1, wherein the reaction is carried out in one step by reacting a reaction mixture comprising an amine or a mixture of two or more amines, or an alcohol or a mixture of two or more alcohols, or a mixture of one or more amines and one or more alcohols, a basic catalyst, formic acid or a salt of formic acid or a mixture of two or more thereof, together with an alkylene oxide or a mixture of two or more different alkylene oxides.

6. A process as claimed in claim 1, wherein the reaction is carried out in two steps, where a) in a first step, a reaction mixture comprising an amine or a mixture of two or more amines, or an alcohol or a mixture of two or more alcohols, or a mixture of one or more amines and one or more alcohols, formic acid or a salt of formic acid, or a mixture of two or more thereof, together with an alkylene oxide, or a mixture of two or more different alkylene oxides, is reacted to form a reaction product of the first step, and b) in a second step, a reaction mixture comprising the reaction product of the first step, a basic catalyst and an alkylene oxide, or a mixture of two or more different alkylene oxides, is reacted.

7. A process as claimed in claim 6, wherein the reaction mixture in the first step comprises an amine or a mixture of two or more amines, where the amine or the mixture of two or more amines is present as an aqueous solution and water is removed essentially completely from the reaction product of the first step before the second step is carried out.

8. A process as claimed in claim 6, wherein the molar ratio of alkylene oxide groups to acidic hydrogen atoms bound to nitrogen in the amine or in the mixture of two or more amines, or in the alcohol or in the mixture of two or more alcohols, or in the mixture of one or more amines and one or more alcohols, in the first step is from 0.6:1 to 0.9:1.

9. A process as claimed in claim 1, wherein the alkoxylated reaction product is maintained at from 40° C. to 140° C. and a pressure of from 0.1 to 100 mbar for a period of from 5 minutes to 5 hours after conclusion of the reaction.

10. A process as claimed in claim 1, wherein the amount of basic catalyst in the reaction mixture is from 0.1 to 20 mol %, based on acidic hydrogen atoms bound to nitrogen in the amine or in the mixture of two or more amines, or in the alcohol or in the mixture of two or more alcohols, or in the mixture of one or more amines and one or more alcohols.

* * * * *